(12) United States Patent
Matthias

(10) Patent No.: US 12,702,974 B2
(45) Date of Patent: Aug. 11, 2026

(54) TEST STRIP ASSEMBLY WITH CONTAINERS

(71) Applicant: Aeneas GmbH & Co. KG, Wendelsheim (DE)

(72) Inventor: Torsten Matthias, Flonheim (DE)

(73) Assignee: Aeneas GmbH & Co. KG, Wendelsheim (DE)

( * ) Notice: Subject to any disclaimer, the term of this patent is extended or adjusted under 35 U.S.C. 154(b) by 25 days.

(21) Appl. No.: 17/731,585

(22) Filed: Apr. 28, 2022

(65) Prior Publication Data

US 2022/0347673 A1 Nov. 3, 2022

(30) Foreign Application Priority Data

Apr. 29, 2021 (DE) .......................... 102021111102.1

(51) Int. Cl.

*B01L 9/00* (2006.01)
*B01L 3/00* (2006.01)
*G01N 33/52* (2006.01)

(52) U.S. Cl.

CPC ............. *B01L 3/5023* (2013.01); *B01L 9/527* (2013.01); *G01N 33/521* (2013.01);
(Continued)

(58) Field of Classification Search

CPC .... B01L 3/5023; B01L 9/527; B01L 2200/16; B01L 2300/021; B01L 2300/044; B01L 2300/069; B01L 2300/168; B01L 9/06; B01L 3/523; B01L 3/527; B01L 3/5453; B01L 3/5457; B01L 2300/0851; B01L 3/50855; B01L 3/50; B01L 9/00; B01L 3/52; B01L 3/502; G01N 33/521; G01N 35/00; G01N 2035/0436

See application file for complete search history.

(56) References Cited

U.S. PATENT DOCUMENTS 8,840,848 B2 * 9/2014 Kraihanzel ............. G01F 23/26 422/417
2002/0155616 A1 * 10/2002 Hiramatsu .............. B01L 3/545 422/400

(Continued)

FOREIGN PATENT DOCUMENTS

CN 102116771 B * 12/2013
EP 1219965 A1 7/2002

(Continued)

OTHER PUBLICATIONS

Extended European Search Report issued on Oct. 24, 2022, in corresponding European Application No. 22167956.6, 18 pages.

*Primary Examiner* — Melvin C. Mayes
*Assistant Examiner* — Sophia Y Lyle
(74) *Attorney, Agent, or Firm* — Buchanan Ingersoll & Rooney PC

(57) ABSTRACT

A test strip system having containers and suitable carriers therefor. The test strip assembly is suitable for carrying out different types of chemical, biological or biochemical tests and evaluating them using a suitable analysis device. The test strip assembly has a first region having at least one container and a second region also having at least one container. The container of the first region has a flat transparent bottom, and the container of the second region has a V-shaped or U-shaped bottom.

20 Claims, 6 Drawing Sheets

(52) U.S. Cl.
CPC ..... *B01L 2200/16* (2013.01); *B01L 2300/021* (2013.01); *B01L 2300/044* (2013.01); *B01L 2300/069* (2013.01); *B01L 2300/168* (2013.01)

(56) References Cited

U.S. PATENT DOCUMENTS

| | | | | |
|---|---|---|---|---|
| 2005/0013746 | A1 | 1/2005 | Lee et al. | |
| 2006/0120926 | A1 | 6/2006 | Takada et al. | |
| 2008/0095670 | A1* | 4/2008 | Gebrian | G01N 35/1002 422/400 |
| 2008/0274451 | A1* | 11/2008 | Bopp | B01L 3/50855 435/5 |
| 2009/0221059 | A1* | 9/2009 | Williams | B01L 7/52 422/400 |
| 2013/0137087 | A1* | 5/2013 | Wilson | G01F 23/24 435/6.12 |
| 2013/0331286 | A1* | 12/2013 | Sappenfield | B01L 3/50855 506/9 |
| 2014/0377785 | A1* | 12/2014 | Janetzko | B01L 3/508 422/69 |
| 2017/0152130 | A1* | 6/2017 | Kakuda | B01L 3/50825 |
| 2017/0266666 | A1* | 9/2017 | Lentz | G01N 35/10 |
| 2019/0360902 | A1* | 11/2019 | Darsigny | G01N 21/76 |
| 2021/0003597 | A1 | 1/2021 | Gorin et al. | |
| 2022/0143618 | A1* | 5/2022 | Wharry | B01L 3/5085 |

FOREIGN PATENT DOCUMENTS

| | | | |
|---|---|---|---|
| EP | 1619130 | A1 | 1/2006 |
| EP | 2073017 | A1 | 6/2009 |
| WO | 2013068760 | A2 | 5/2013 |
| WO | 2013068760 | A3 | 5/2013 |

* cited by examiner

Fig. 3a
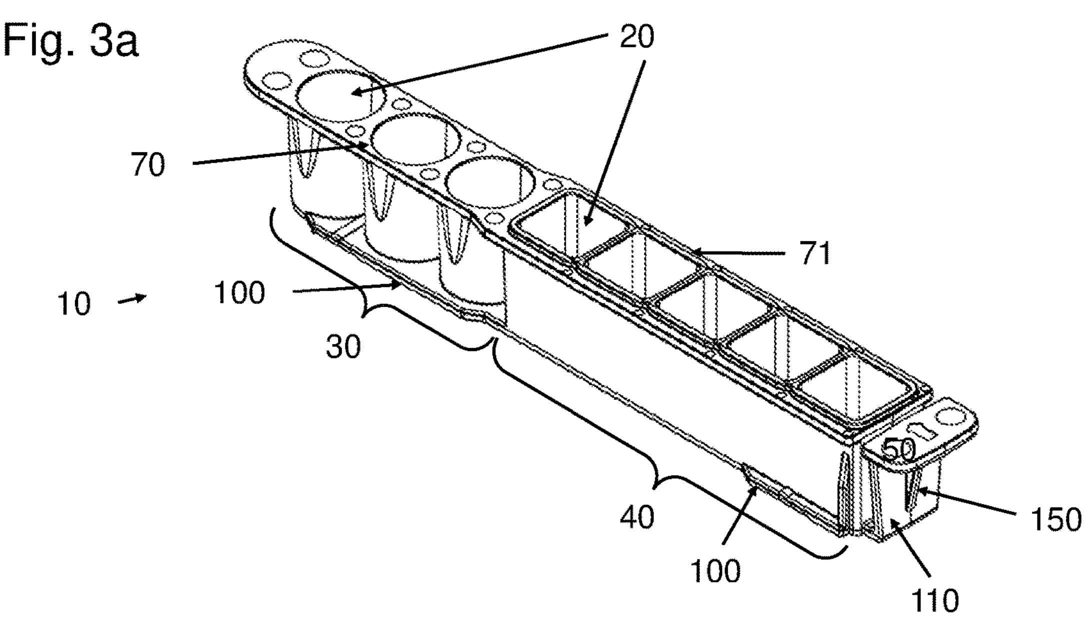
Fig. 3b
Fig. 3c
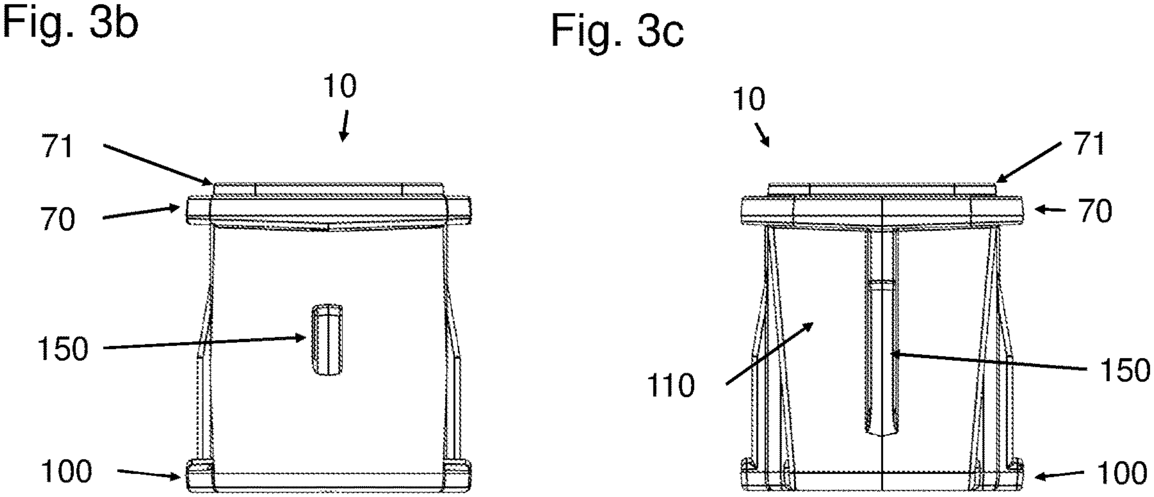
Fig. 3d
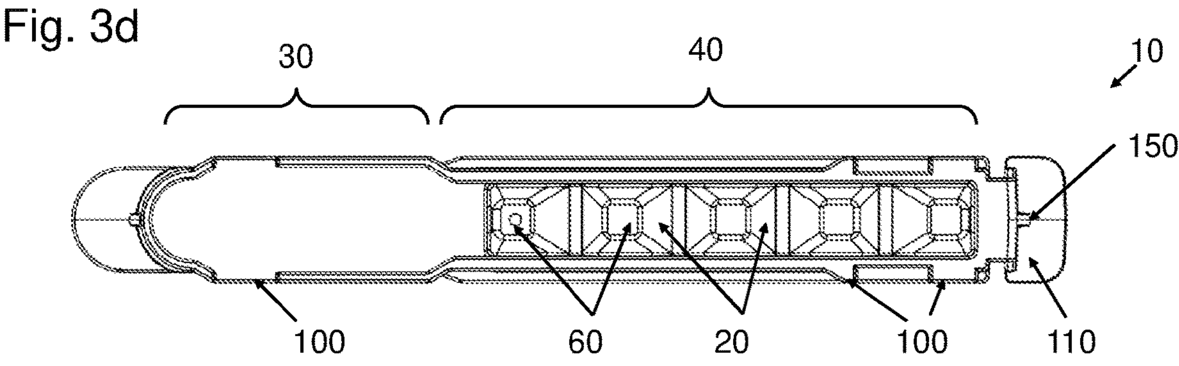

120
140
140
160
140
140
130

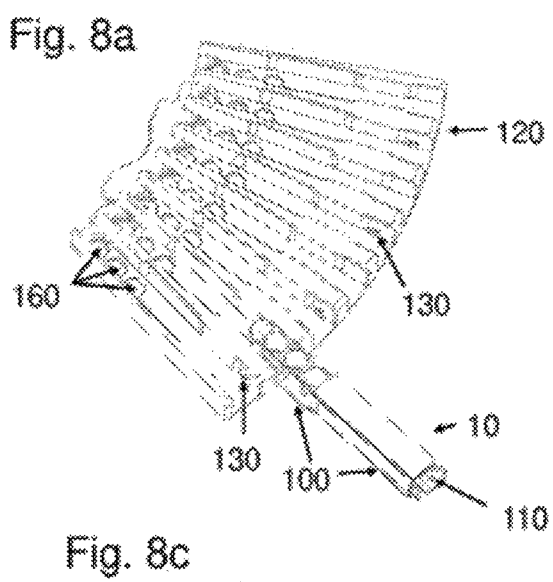
Fig. 8a
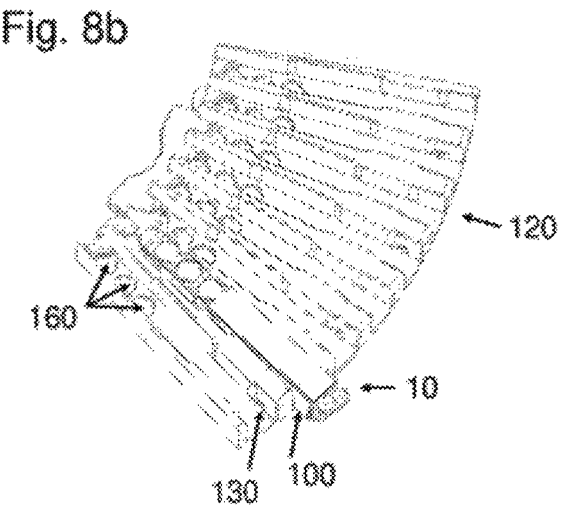
Fig. 8b
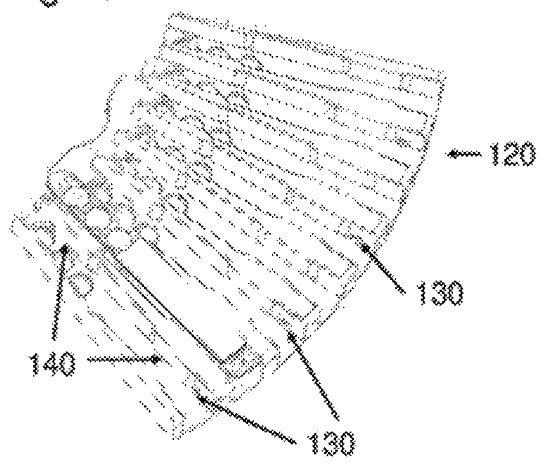
Fig. 8c
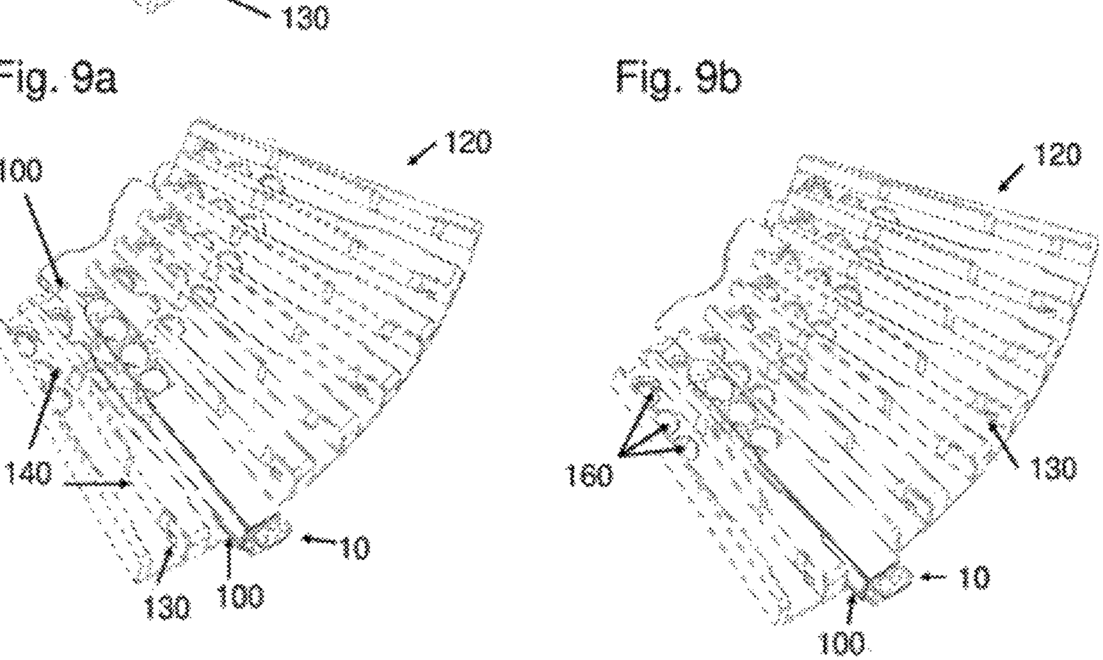
Fig. 9a
Fig. 9b

TEST STRIP ASSEMBLY WITH CONTAINERS

FIELD

The invention relates to a test strip system having containers and suitable carriers for this purpose. The test strip assembly is suitable for carrying out various types of chemical, biological, or biochemical tests and evaluating them using a suitable analysis device.

BACKGROUND

A large number of such test strip systems are known from the prior art. Most of these test strip systems have a uniform shape, however, i.e., a uniformly formed number of containers is provided, which are arranged in succession and are usually connected to one another by small webs or bridges. Such assemblies are often used in analytical and diagnostic laboratories, inter alia, in PCR polymerase chain reaction systems, or are used as reaction containers for detecting ELISAs. The strip systems are, inter alia, colored white or black or are transparent here, so that reactions stimulated by reagents or also reactions stimulated by light or other radiation can be made visible within a container of the test strip or can be analyzed, for example, by means of suitable filters. The containers which contain such a test strip system are usually of the same geometric design. The containers usually have a conical and semicircular shape in the region of the bottom or are completely flat in the region of the bottom and have a cylindrical configuration. A conical and semicircular shape has the advantage of wasting or losing little sample volume or also volume of the test reagents when mixing the reagents or when starting an experiment. However, a conical and semicircular shape is not particularly well suitable for detection, since stray light, interference, or similar phenomena can occur in the region of the conically shaped bottom. In addition, the container bottoms are usually also provided with special non-biological or biological coatings, such as antibodies or antigens or the like, which in turn is sometimes more difficult or almost impossible with a conical shape. In addition, an evaluation of, for example, fluorescence events or color changes when coating a conical shape is difficult or even impossible.

SUMMARY

The invention therefore has the object of improving test strip assemblies having cavities, primarily those which are used to analyze samples or reagents.

In particular, an arrangement is to be provided in which the reagents or samples used are processed with as little loss as possible.

A further object is to provide efficient and qualitative analysis conditions. In this case, in particular, efficiency in terms of the ability to be evaluated and to carry out various analysis methods such as colorimetry, photometry, fluorescence, chemiluminescence, electrochemiluminescence, and the like are to be provided.

A further object is to provide a test strip assembly having cavities that allows easy handling, in particular with regard to carrying out the experiments or tests with regard to safety, likelihood of confusion, and easier handling.

A further object of the invention is also to make the test strip assembly available as a kind of "ready-to-go" test assembly which stores all the reagents required for a test and has high long-term stability in terms of storage.

The objects are achieved by a test strip assembly having cavities and a carrier suitable therefor according to independent claims 1 and 10. Advantageous refinements and preferred embodiments are specified in the dependent claims.

The test strip assembly having cavities according to the invention comprises a first region having at least one container and a second region also having at least one container. The case here is that the container of the first region has a flat, transparent bottom and the container of the second region has a predominantly V-shaped or predominantly U-shaped bottom. The container of the first region is also referred to as the reaction or dilution container within the meaning of the invention. A reagent can be applied in the container of the second region or is already present there, using which a test can be carried out. In the case of complex tests, the test strip assembly having containers according to the invention can also have additional containers in the second region. Depending on what kind of test is involved, different reagents from the different containers of the second region can then be mixed in succession, if necessary, in order to then carry out a test. A container in the second region can optionally contain a buffer solution, and a further container in the second region can then contain special marking agents or other reagents, etc. In the context of the invention, a container can also be understood to mean a recess or cavity that is able to accommodate a fluid, primarily a liquid, and to store it at least temporarily.

The bottom shape according to the invention of the container of the second region allows the contents of the container to be accommodated almost completely, as a result of which almost no residues remain and the test is thus carried out reliably.

Due to the bottom shape according to the invention of the container of the first region, which is flat and transparent, an analysis of the reagents or samples can be carried out well and reproducibly using suitable analysis devices. Suitable analysis methods that can be used here are, for example, colorimetric, photometric, spectrometric, and light microscopic methods, ELISAs, colorimetry, photometry, fluorescence, chemiluminescence, electrochemiluminescence, and other methods.

According to an advantageous embodiment of the test strip assembly, the containers provided with reagents in the second region are covered with a film and sealed for security against contamination or evaporation or for security against spilling.

According to a further advantageous embodiment of the test strip assembly having containers, the film with which the second region is covered is manufactured in such a way that this film can be pierced using a pipette tip. Furthermore, the film is made of a material that is suitable for sealing the test strips. In this case, the film can be firmly connected to the test strip by a suitable material or by a suitable method. Suitable materials would be, for example, an adhesive, glue, or polymer having a high affinity for the test strip material and low vapor permeability, which is suitable for stable long-term storage, or a method such as welding using heat or light. The film can be single-layer or multi-layer and equipped with a carrier material, e.g., a polymer, light metal, or other materials. The film material also preferably has properties which generally ensure the leak-tightness and durability as well as the stability of the film and the reagents.

According to an advantageous embodiment of the test strip assembly having containers according to the invention, the containers of the first and second regions have a rim. According to the invention, the rim of the second region is taller than that of the first region. In this case, the rim of the second region is advantageously 0.2 mm taller than the rim of the first region. The rim of the second region is preferably 0.4 mm taller than the rim of the first region and the rim is particularly preferably 0.6 mm taller than that of the first region. An advantageous difference between the rim of the first region and the rim of the second region has been found with a 0.5 mm taller rim of the second region. Due to the slightly taller rim of the second region compared to the first region, significantly improved welding or adhesive bonding of the film to the test strip assembly is possible. This ensures better leak-tightness for longer shelf life and stability. In addition, there is also the high vapor barrier of the entire test strip assembly and the film material, so that the reagents can also be stored stably for a long time.

According to a further advantageous embodiment of the test strip assembly having containers according to the invention, with the exception of the bottom of the first region, it is made of an opaque, translucent, or transparent material. Materials which are primarily used for this purpose are thermoplastics such as polyethylene, polypropylene, polyamide, polymethyl methacrylate, or polystyrene. Thermoset plastics are also suitable for this purpose, such as melamine-formaldehyde resin (phenoplasts) or UF aminoplasts. However, it is also conceivable to use glass or glass silicates as well as ceramics for this purpose.

According to a further advantageous embodiment, a cyclo-olefin polymer (COP) or a cyclo-olefin copolymer (COC) is used, wherein these materials are characterized by particular durability, high optical transmission in the visual spectral range, low inherent fluorescence, low water absorption, and low vapor permeability.

It is also possible that the containers of the first region are made of one material and the cavities of the second region have a different material, depending on which test conditions are to prevail at the time. Advantageously, the containers of the second region can be made entirely or partially of an opaque, translucent, or transparent material.

According to a further advantageous embodiment of the test strip assembly having containers according to the invention, it has a barcode or a marking for identifying the test strip assembly. Such a barcode or a marking can be, for example, a barcode, QR code, RFID code, or any other typical barcode or marking. The barcode contains as information, among other things, the composition of the reagents which can be present in the test strip assembly and can therefore provide information about the shelf life of the reagents if they are stored at a specific temperature and condition. Furthermore, such a barcode can uniquely identify the test strip assembly provided with it, which is intended to prevent test results from being confused or mixed up later. In addition, such a barcode can easily be registered and read by a reader provided for this purpose, so that a unique assignment of the test strip assemblies, for example, to a specific patient or test is ensured, wherein for non-authorized persons the barcode cannot be assigned to a specific test or a specific person on the basis of its appearance. This ensures anonymized performance of tests and their further storage.

According to a further advantageous embodiment of the test strip assembly having cavities according to the invention, it has guide webs laterally at the lower end of the test strip assembly, more precisely laterally to the bottom of the first and second region. These guide webs are used so that the test strip can be positioned precisely in a carrier provided for this purpose and can be detachably fixed in a form-fitting manner, in order to enable, for example, pipetting, washing, and evaluating of the tests and ejecting of the test strip from the carrier.

According to a further advantageous embodiment of the test strip assembly having containers according to the invention, viewed from above, it tapers from the first region toward the second region or the second region has a section in which no guide webs extend. According to a further embodiment, the side surfaces of the second region are continuously provided with material, resulting in side surfaces that ensure better haptics of the test strip assembly in the second region. Furthermore, the above-described embodiments of the test strip assembly and a carrier shape adapted to the shape of the test strip assembly mean that the test strip assembly can only be arranged in a very specific direction or a specific way in a carrier. This prevents, for example, an unintentional mixup of the first with the second region, so that the test strip assembly cannot be inserted incorrectly, for example into an analysis device, as a result of which application errors are practically ruled out.

According to a further advantageous embodiment of the test strip assembly having containers according to the invention, it has a clamp having a clamping spring on one side. This clamping having a clamping spring has the advantage that the test strip assembly can be inserted into a carrier provided for this purpose and remains there securely. This connection can be released again by pressing the springs with almost no force or with little force by displacing the test strip in the carrier, as a result of which the test strip assembly can be detached again from the carrier provided for this purpose.

According to a further advantageous embodiment of the test strip assembly having containers according to the invention, the test strip assembly has at least one reagent in at least one container of the second region and/or a coating in at least one cavity of the first region. In this case, the coating is advantageously restricted to the bottom of the cavity. In terms of the invention, coating is also understood to mean vapor deposition, printing, painting, spraying, and/or incubation. In the context of the invention, the coating here primarily represents a non-biological or biological coating, such as an antibody, an antigen, a sample such as blood or urine, a specific chemical substance, a specific biological substance, DNA or RNA. In an exemplary test scenario, a sample can then be applied in the container of the first region, for example. One or more reagents from the containers in the second region are then added, which triggers a reaction which can then be analyzed in the cavity of the first region by means of suitable analytical instruments.

Furthermore, the invention also comprises a carrier for an above-described test strip assembly. The carrier according to the invention for a test strip assembly having containers is designed in such a way that the test strip assembly is releasably fixed within the carrier by means of a clamp and/or by means of guide webs which are pushed into guide rails of the carrier provided for this purpose. According to the invention, the test strip assembly can be introduced into the carrier with the clamp having clamping spring and fixed on the carrier by a slight force on the spring. However, it is also possible again to detach the test strip assembly from the carrier again by applying a slight force to the spring. According to the invention, however, the carrier can also be designed in such a way that the test strip assembly is pushed into the carrier, wherein the carrier has suitable guide rails or recesses for this purpose.

According to an advantageous embodiment of the carrier according to the invention for a test strip assembly, it has an additional spring, as a result of which the test strip assembly, which is inserted into the guide rails of the carrier provided for this purpose by means of the webs, is also releasably fixed on the carrier. Such a spring can be formed, for example, by a slightly bent metal strip. In this way, a slight force is exerted on one side of the test strip assembly. The force is just great enough to hold the test strip assembly in the carrier precisely and stably. However, the force is only so great that it is still possible for the user to displace the test strip assembly for supply or removal.

According to a further advantageous embodiment of the carrier according to the invention for a test strip assembly, the carrier is in the form of a rectangle, a full circle or semicircle, or a segment of a circle. In principle, the carrier can be designed in any geometric shape with the proviso that the carrier has a shape suitable for analysis by an analysis device.

According to a further advantageous embodiment of the carrier according to the invention for a test strip assembly, the carrier has a suitable complementary shape in order to function as a carrier unit in an analysis device suitable for this purpose.

The test strip assembly having containers according to the invention and the carrier according to the invention for such a test strip assembly are described in more detail hereinafter in exemplary embodiments and in drawings. The explanations are merely exemplary and do not restrict the general concept of the invention.

BRIEF DESCRIPTION OF THE FIGURES

In the figures:

FIG. 3*a* shows a schematic representation of an embodiment of the test strip assembly 10 according to the invention in a perspective view;

FIG. 3*b* shows a schematic representation of an embodiment of the test strip assembly 10 according to the invention in a front view;

FIG. 3*c* shows a schematic representation of an embodiment of the test strip assembly 10 according to the invention in a rear view;

FIG. 3*d* shows a schematic representation of an embodiment of the test strip assembly 10 according to the invention from below;

FIG. 8*a* shows a schematic representation of the sequence of inserting a test strip assembly 10 according to the invention into an embodiment of a carrier according to the invention;

FIG. 8*b* shows a schematic representation of the sequence of inserting a test strip assembly 10 according to the invention into an embodiment of a carrier according to the invention;

FIG. 8*c* shows a schematic representation of the sequence of inserting a test strip assembly 10 according to the invention into an embodiment of a carrier according to the invention;

FIG. 9*a* shows a further schematic representation of a further possibility of equipping the carrier according to the invention from FIG. 8 with a test strip assembly 10 also from FIG. 8;

FIG. 9*b* shows a further schematic representation of a further possibility of equipping the carrier according to the invention from FIG. 8 with a test strip assembly 10 also from FIG. 8.

DETAILED DESCRIPTION

Figure 1:
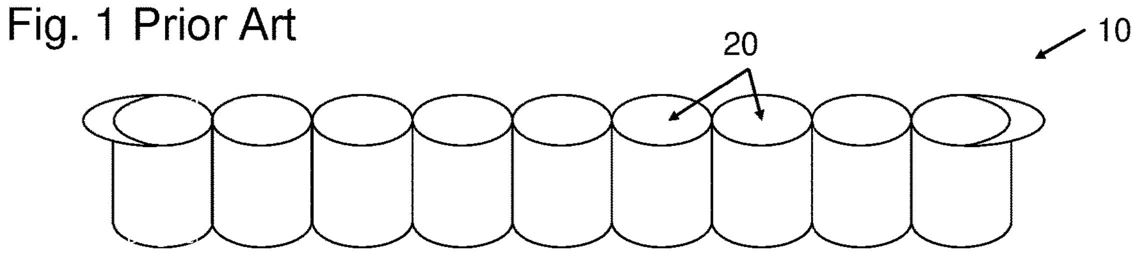
FIG. 1 shows a schematic representation of a test strip assembly 10 according to prior art in a perspective view.

FIG. 1 shows a test strip assembly 10 according to the prior art. It is clear here that all containers 20 of the test strip assembly 10 have a flat bottom. Furthermore, this test strip can also be used in a holder provided for this purpose, but it then only fits loosely. A further disadvantage of this test strip assembly 10 according to the prior art is that the test strip can be inserted upside down in the carrier and it is thus possible to mix up the sample or the assignment of the sample to a specific patient or reference value can be mixed up. A further disadvantage is that the test strip assembly 10 according to the prior art cannot be releasably fixed in a carrier. For example, air bubbles, which could interfere with the detection reaction, cannot be knocked out manually or automatically.

Figure 2A:
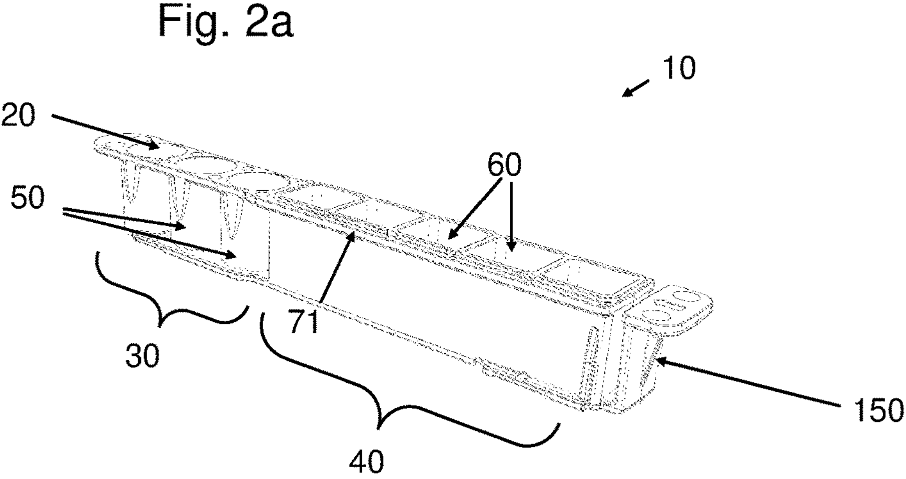
FIG. 2*a* shows a schematic representation of an embodiment of the test strip assembly 10 according to the invention in a perspective view.

FIG. 2*a* shows a perspective schematic representation of an embodiment of the test strip assembly 10 according to the invention. The test strip assembly 10 shown has a transparent, see-through material. The materials can be selected depending on the application, so that, for example, a black material reduces scattered light or interference, while other materials in turn have other properties.

Clamping springs 110 for forming a clamp with a suitable carrier according to the invention can also be seen. Furthermore, FIG. 3*a* also shows the guide webs 100, which are also used to guide and fix the test strip assembly 10 according to the invention in a suitable carrier. Furthermore, a first region 30 having rather cylindrical containers 20 and a second region 40 having rather cuboid containers 20 can be seen in FIG. 2*a*. It can also be seen that the second region 40 has a taller rim 71 than the first region.

Figure 2B:
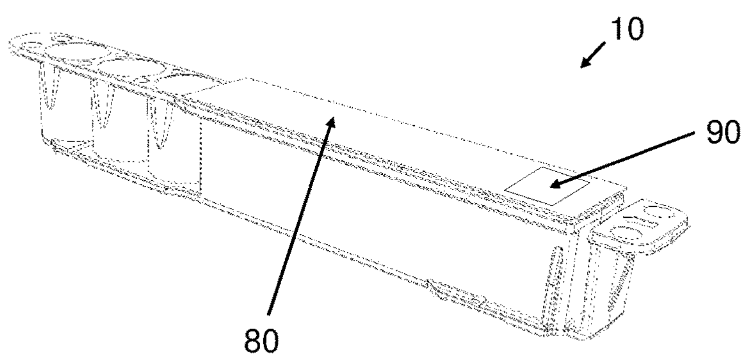
FIG. 2*b* shows a schematic representation of an embodiment of the test strip assembly 10 according to the invention in a perspective view with film.

FIG. 2*b* shows the test strip assembly 10 according to the invention, already known from FIG. 2*a*, having a film 80. The cover film 80 is applied to the slightly taller rim 71 of the container 20 of the second region. The film 80, also known as the sealing film, is conceived in such a way that it can be easily pierced using pipette tips. Furthermore, the film 80 has a coating that is designed in such a way that it burns up little and can be structured, inscribed, or printed on.

The film 80 also makes it possible to use the test strip assembly 10 as a type of storage container having an integrated test device at the same time. For this purpose, one or more reagents are poured into one or more containers 20 of the second region 40 and sealed using the above-mentioned film 80. This can be done, for example, by welding or adhesive bonding. The protruding rim 71 of the cavities 20 of the second region 40, which preferably has a height of 0.5 mm, achieves a significantly better fastening the cover film 80 to the test strip assembly 10 than is conventionally the case. In this way, a better leak-tightness for longer shelf life and stability of the reagents stored in the test strip assembly 10 can be ensured and achieved. In addition, the test strip and film material has a high vapor barrier, which means that the reagents can be stored with long-term stability. The cavities 20 of the first region 30, also called reaction or dilution cavities 20, can be coated using a product-specific antigen, antibody, or other proteins or chemicals in a further production step. If, for example, such a reaction cavity or a reaction container is coated using a product-specific antigen, a specific antibody present in the patient serum, for example, can be detected. However, not only patient sera but also other analytes such as urine or CSF (cerebrospinal fluid) can be used. In addition, in this example the film 80 has a barcode 90 which ensures a unique and at the same time anonymized assignment of test and sample.

FIG. 3*a* shows an embodiment of the invention in which the first region 30 having three containers 20 and the second region 40 having five containers 20 can be clearly seen. The containers 20 of the first region 30 here have a cylindrical configuration, while the containers 20 of the second region 40 show a rather cuboid configuration. The clamping spring 110 having the lug 150 can also be seen, which is used to temporarily fix the test strip assembly 10 in a carrier. The side surfaces in the second region 40 are designed to be flat, which allows easier and more convenient handling for the user, for example when inserting the arrangement into a carrier. FIG. 3*b* and FIG. 3*c* show the front and rear view of an embodiment of the test strip assembly 10 according to the invention. The lugs 150, which are used for fixing in the carrier, and the raised rim 71 for the application of a film 80 in the second region 40 can be clearly seen. FIG. 3*d* shows a bottom view of one embodiment of the test strip assembly 10 of the present invention. The guide webs 100 on the bottom in the first region 30 and in the second region 40 can be seen here above all.

Figure 4A:
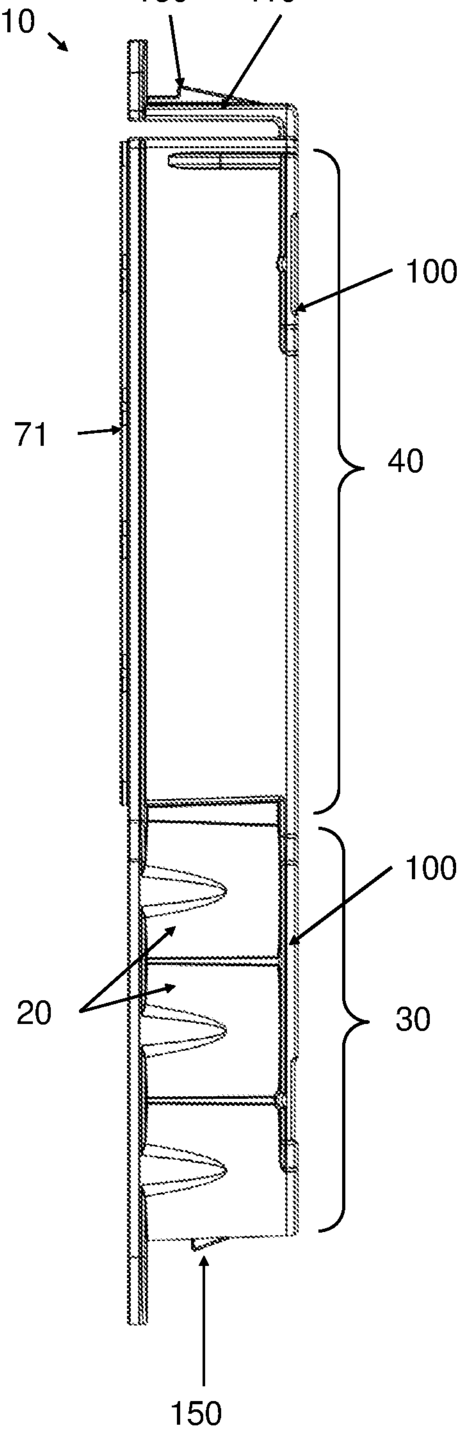
FIG. 4*a* shows a schematic representation of an embodiment of the test strip assembly 10 according to the invention from FIG. 3 in a side view.

FIG. 4*a* shows a schematic representation of an embodiment of the test strip assembly 10 according to the invention in a side view. The clamping with the clamping spring 110 can be clearly seen, which additionally has a small lug 150 formed from the material of the test strip assembly 10. A lug 150 can also be seen on the opposite side of the clamping spring 110. These lugs 150, together with the likewise opposing handles, enable the test strip assembly 10 according to the invention to be securely fixed in a carrier 120 suitable for this purpose. The slightly raised rim 71 of the cavities 20 in the second region 40 in contrast to the cavities 20 of the first region 30 can also be seen.

Figure 4B:
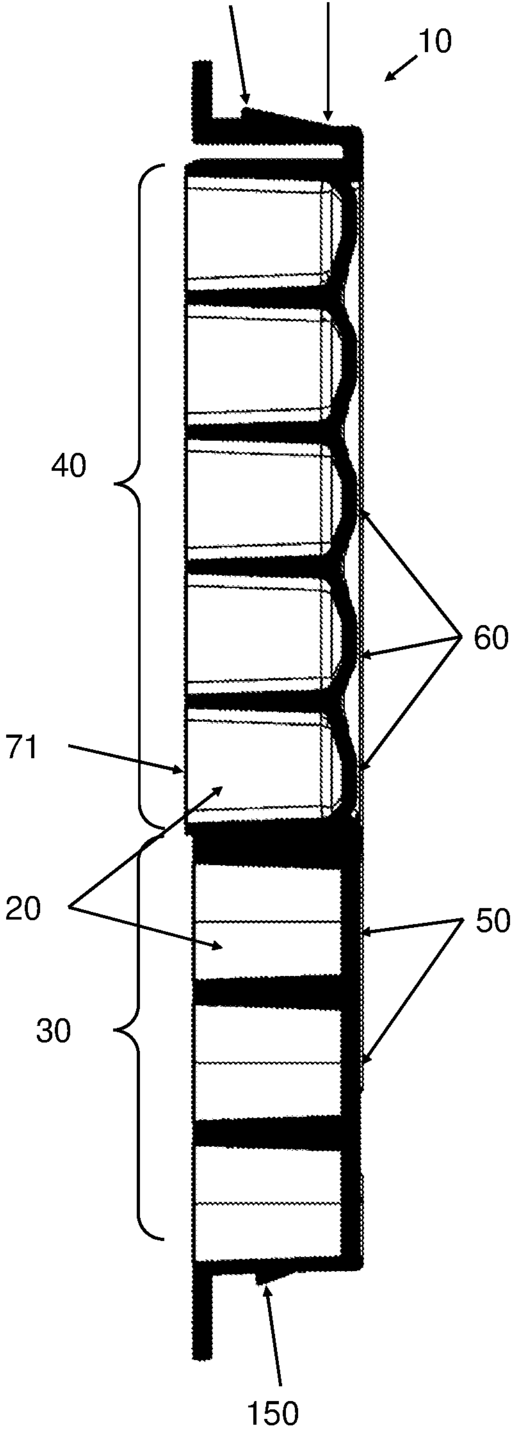
FIG. 4*b* shows a schematic representation in a side view of a sectional plane of the embodiment of the test strip assembly 10 according to the invention from FIG. 4*a;*

FIG. 4*b* shows an embodiment of the test strip assembly 10 according to the invention from FIG. 4*a* in an illustration of a longitudinal section which extends centrally through the test strip assembly 10 from the front to the rear, seen from above. It can be seen that the cavities 20 of the first region 30 have a flat bottom 50, while the cavities 20 of the second region 40 have a rather V-shaped or also U-shaped bottom 60. This bottom shape of the cavities 20 of the second region 40 leaves less dead volume when liquids are removed, which means that less test reagents or other liquids have to be used, which in turn reduces the general costs. The clamp having the clamp spring 110 can also be seen having the small lugs 150 formed from the material of the test strip assembly 10.

Figure 5A:
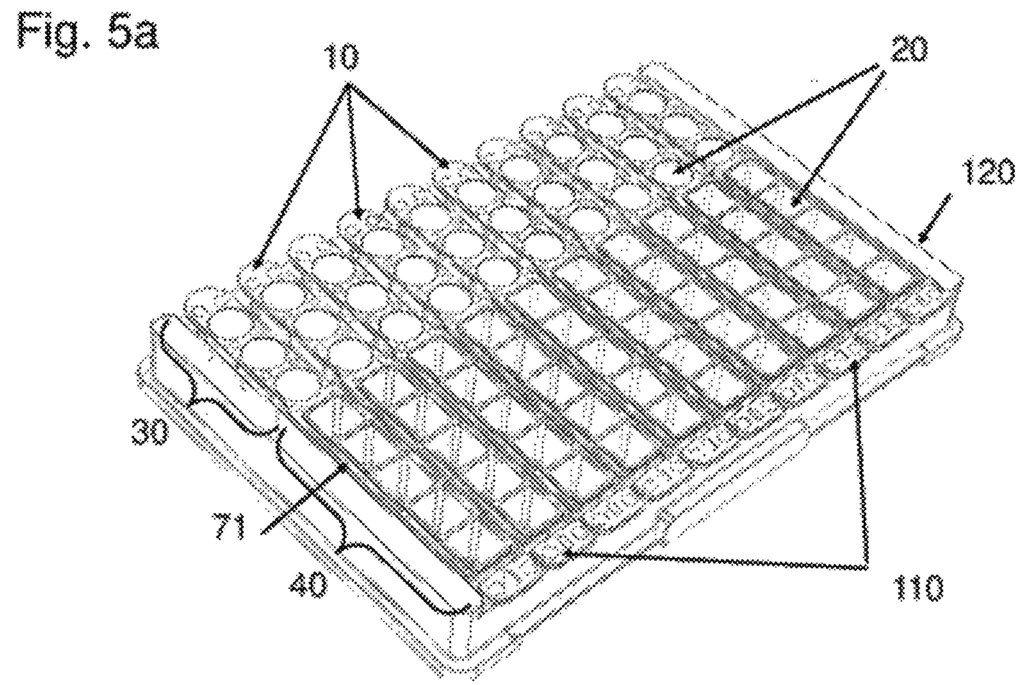
FIG. 5*a* shows a schematic representation in a top view of an embodiment of the test strip assembly 10 according to the invention within an embodiment of a carrier according to the invention.
Figure 5B:
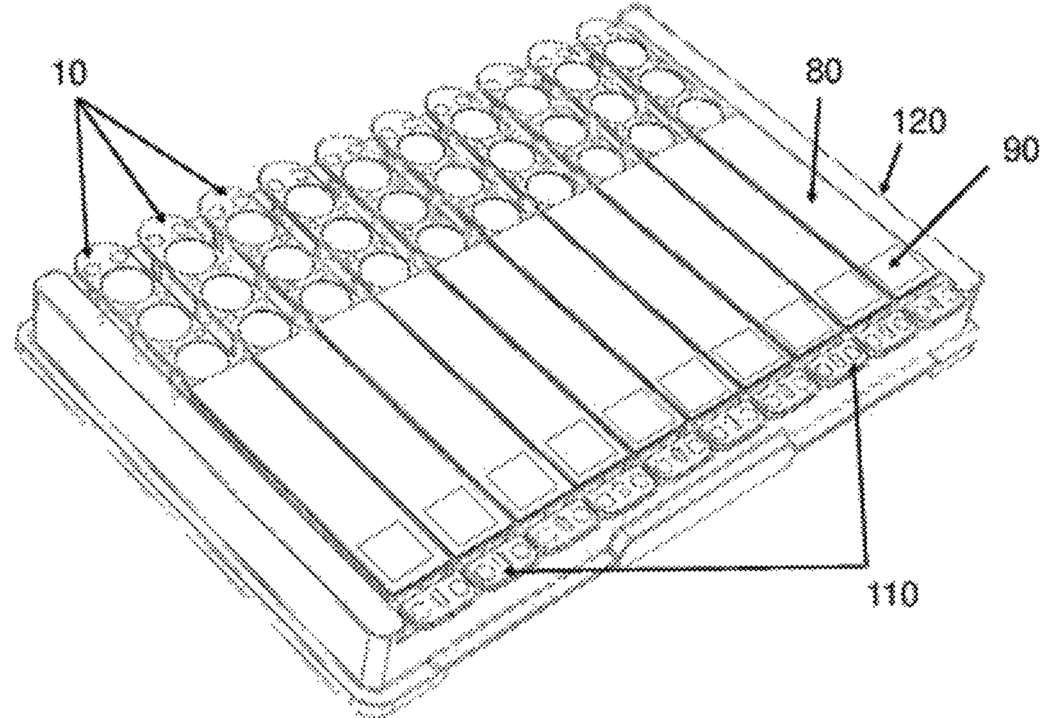
FIG. 5*b* shows a schematic representation in a top view of an embodiment of the test strip assembly 10 according to the invention within an embodiment of a carrier according to the invention.

FIGS. 5*a* and 5*b* show a schematic representation of a carrier 120 according to the invention, which is equipped with embodiments of a test strip assembly 10 according to the invention, once with films 80 (FIG. 5*b*) and without films (FIG. 5*a*). The advantage of such a combination of carrier and test strip assembly is that the individual test strip assemblies 10 can be easily detached from the carrier 120, but the other test strip assemblies 10 can remain stationary in the carrier 120.

As can also be seen in FIG. 3, for example, the test strip assembly 10 tapers somewhat in the first region 30 compared to the second region 40. This tapering enables the test strip assembly 10 to be inserted correctly in the carrier 120 provided for it later and thus offers a high degree of usability. Because of this shape, the test strip assembly 10 can only be inserted in one direction into the carriers 120 provided for this purpose according to the invention, also referred to as frames. Incorrect handling is thus avoided from the outset. The end user removes a test strip assembly 10, for example having prefilled reagents and/or coated reaction or dilution containers 20, from a packaging material provided for this purpose and inserts this test strip assembly 10, for example from the front or from above, into a carrier 120 provided for this purpose. Such a carrier 120 according to the invention having the test strip assembly 10 according to the invention is then positioned in an analysis device and the test is processed automatically or semi-automatically.

Figures 6, 7:
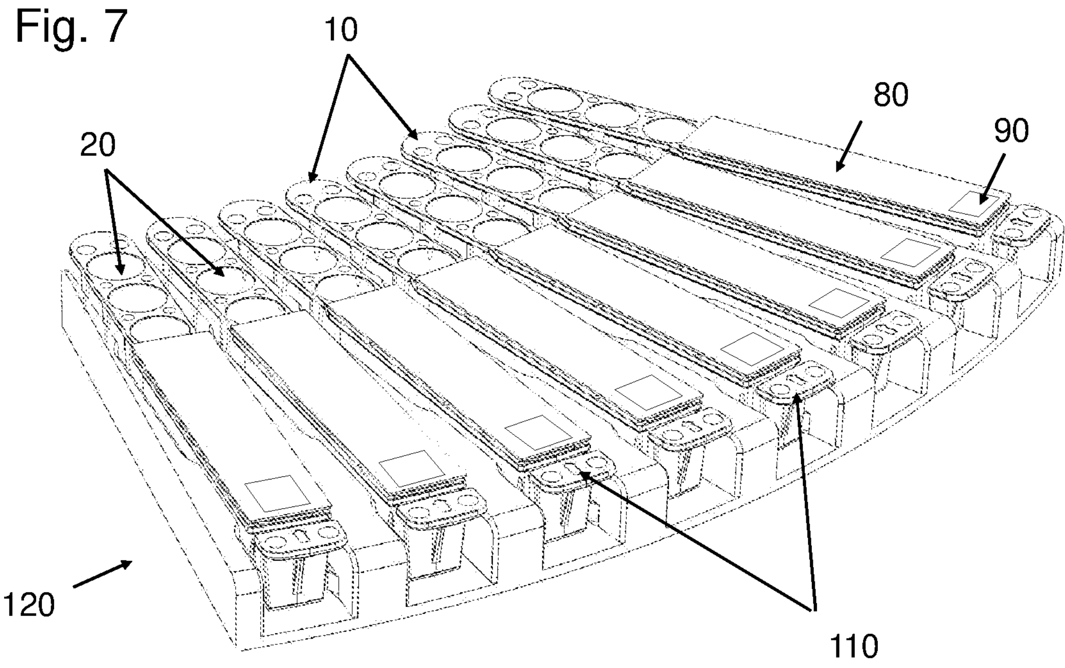
FIG. 6 shows a schematic representation of an embodiment of a carrier according to the invention without test strip assembly 10.
FIG. 7 shows a schematic representation of an embodiment of a carrier according to the invention having inserted test strip assembly 10 having film 80.

FIG. 6, for example, shows a schematic representation of an embodiment of a carrier 120 of the present invention in the shape of a segment of a circle without test strip assemblies 10 of the present invention. The additional spring 130 of the carrier, which can detachably fix the test strip assembly 10 by means of a counterforce, can be seen clearly here. The guide rails 140 or recesses are also visible, into which the guide webs 100 of the test strip assemblies 10 are introduced and thus additionally prevent the test strip assemblies 10 from slipping out of the carrier 120 in an upward direction. It can also be seen that the carrier 120 has recesses in the form of through holes 160 in the region in which the first region 30 of the test strip assembly 10 will later be located. These through holes 160 are provided to ensure the analysis of the tests or test reactions.

FIG. 7 shows a schematic representation of an embodiment of a carrier 120 according to the invention having inserted test strip assemblies 10. Each individual test strip assembly 10 can also be detached separately from the carrier 120 in this embodiment, without the other test strip assemblies 10 being adversely affected as a result.

In the schematic sequence representations in FIGS. 8*a-c*, the insertion of a test strip assembly 10 according to the invention into an embodiment of a carrier 120 according to the invention is shown. Here, the test strip assembly 10 is pushed laterally into the carrier 120 (FIG. 8*a*). The test strip assembly 10 is securely fixed in the carrier by means of the guide webs 100 and the guide rails 140 or recesses provided for this purpose. Due to the tapering of the test strip assembly 10 in the first region 30 and a tapering of the carrier 120 complementary thereto, the test strip assembly 10 can also only be fully pushed into the carrier 120 in one direction. The additional spring 130, which is installed in the carrier 120, protects the test strip assembly 10 from slipping out. However, this clamping connection can be released again by the end user with little force, so that the test strip assembly 10 can be removed from the carrier 120 again.

FIGS. 9*a* and 9*b* each show a further schematic representation of a possibility of equipping the carrier 120 according to the invention from FIG. 8 with a test strip assembly 10. For this purpose, the test strip assembly 10 is introduced into the carrier 120 from above. Due to the mentioned tapering in the second region 40 of the test strip assembly 10 and the complementary shape of the carrier 120, the test strip assembly 10 can only be inserted into the carrier in one direction from above. In the last step of this procedure, the test strip assembly 10 is again pushed forward with little force in order to be protected from slipping out by the additional spring 130 installed on the carrier 120. The guide elements close to the bottom such as the guide rail 140 or recess of the carrier 120 and the webs 100 of the test strip assembly 10 enable precise guiding and positioning of the test strip assembly 10 during pipetting, washing, evaluating, and ejecting of the test strip assembly 10 or the tests located therein. The additional springs or spring clamping elements 110 enable simple installation, removal, and supply of the entire test strip assembly 10. Likewise, by means of the spring 130 provided on the carrier 120, the test strip assembly 10 can snap into place in the carrier 120 in an audible and perceptible manner for the user, in order to ensure that the test strip assembly 10 has been correctly inserted into the carrier 120.

LIST OF REFERENCE NUMERALS

10 test strip assembly
20 containers
30 first region
40 second region
50 transparent bottom
60 V-shaped or U-shaped bottom
70 rim
71 rim of the second region
80 film
90 bar code
100 guide webs
110 clamp having clamping spring
120 carrier
130 spring
140 guide rail
150 lug
160 through hole

The invention claimed is:

1. A test strip assembly comprising containers, wherein the test strip assembly has a first region having at least one first container of the containers and a second region also having at least one second container of the containers; wherein the at least one first container of the first region has a flat transparent bottom and is configured to retain patient fluid therein for analysis via at least one analysis device and the at least one second container of the second region has a V-shaped or U-shaped bottom and is configured to retain liquid having a buffer solution and at least one reagent therein, the at least one second container of the second region also configured to receive a distal end of a pipette therein;

wherein the at least one first container in the first region and the at least one second container in the second region are made of different materials, the at least one first container being cylindrical and the at least one second container being cuboid;

the test strip assembly having a first side and a second side opposite the first side, the first region being adjacent the first side and the second region being adjacent the second side, the first side having a rounded end and the second side being wider than the rounded end of the first side;

a clamping spring being positioned on the second side of the test strip assembly to releasably couple the test strip assembly to a carrier; and the test strip assembly tapering in the second region and also tapering in the first region as compared to the second region such that the test strip assembly tapers as the test strip assembly extends from the second region to the first region.

2. The test strip assembly as claimed in claim 1, wherein the containers of the first and the second region each has a rim, wherein the rim of the containers of the second region is taller than the rim of the containers of the first region and the at least one second container of the second region is closed using a film that is bonded to the rim of the containers of the second region.

3. The test strip assembly as claimed in claim 2, wherein the test strip assembly or the film has a barcode for identifying the test strip assembly.

4. The test strip assembly as claimed in claim 2, wherein the film is manufactured in such a way that it can be pierced using a pipette tip.

5. The test strip assembly as claimed in claim 1, wherein the test strip assembly, with the exception of the bottom of the at least one first container of the first region, consists of an opaque material, light-transmitting material, or transparent material and the bottom of the at least one first container of the first region is comprised of a transparent material.

6. The test strip assembly as claimed in claim 1, wherein the second region consists of a light-transmitting material, or transparent material.

7. The test strip assembly as claimed in claim 1, wherein the test strip assembly has lateral guide webs.

8. The test strip assembly as claimed in claim 1, wherein the second region has guide webs and the first region has guide webs and wherein a section of the second region does not include the guide webs of the second region.

9. The test strip assembly as claimed in claim 1, wherein the test strip assembly has a lug adjacent the clamping spring.

10. The test strip assembly as claimed in claim 1, wherein the test strip assembly has test reagents which are located in the at least one second container of the second region and are sealed by a film bonded to a rim of the containers of the second region.

11. The test strip assembly as claimed in claim 1, also comprising the carrier, wherein the test strip assembly is releasably fixed in the carrier by the clamping spring.

12. The test strip assembly as claimed in claim 11, wherein the carrier additionally has an additional spring, by which the test strip assembly, which was introduced into the carrier by guide webs of the first region and guide webs of the second region, is additionally releasably fixed to the carrier via the additional spring engaging the test strip assembly adjacent the second region, the guide webs of the first region and the guide webs of the second region being pushable into guide rails of the carrier.

13. The test strip assembly as claimed in claim 11, wherein the carrier is in the form of a rectangle, a circle, or a segment of a circle.

14. The test strip assembly as claimed in claim 1, wherein the at least one second container in the second region is entirely made of an opaque material.

15. The test strip assembly as claimed in claim 1, wherein the at least one first container of the first region has a rim and the at least one second container of the second region has a rim that is taller than the rim of the at least one first container of the first region.

16. The test strip assembly as claimed in claim 15, wherein the at least one second container of the second region is closed using a film that is pierceable by the pipette so the pipette can pierce the film and be positioned within the at least one second container, the film being bonded to the rim of the at least one second container of the second region.

17. The test strip assembly as claimed in claim 16, wherein the at least one second container of the second region is also configured to retain at least one marking agent therein.

18. The test strip assembly as claimed in claim 17, wherein the film has a barcode for identifying the test strip assembly.

19. The test strip assembly as claimed in claim 1, wherein the first region of the test strip assembly has guide webs.

20. The test strip assembly as claimed in claim 1, wherein the second region has a section in which no guide webs extend.

* * * * *